United States Patent [19]
Amselem

[11] Patent Number: 5,891,469
[45] Date of Patent: Apr. 6, 1999

[54] SOLID COPRECIPITATES FOR ENHANCED BIOAVAILABILITY OF LIPOPHILIC SUBSTANCES

[75] Inventor: Shimon Amselem, Rehovot, Israel

[73] Assignee: Pharmos Corporation, New York, N.Y.

[21] Appl. No.: 833,076

[22] Filed: Apr. 2, 1997

[51] Int. Cl.6 ............................. A61K 9/48; A61K 9/20
[52] U.S. Cl. ..................... 424/451; 424/439; 424/452; 424/464; 424/465; 424/489; 424/502; 514/458; 514/960
[58] Field of Search ................... 424/451, 439, 424/452, 464, 465, 489, 502; 514/458, 960; 549/408

[56] References Cited

U.S. PATENT DOCUMENTS

| | | | |
|---|---|---|---|
| 3,102,078 | 8/1963 | Robeson | 514/458 |
| 3,673,163 | 6/1972 | Walkling | 514/285 |
| 4,327,080 | 4/1982 | Wong et al. | 514/224.2 |
| 4,412,986 | 11/1983 | Kawata et al. | 514/356 |
| 4,562,069 | 12/1985 | Hegasy et al. | 514/356 |
| 4,578,391 | 3/1986 | Kawata et al. | 514/256 |
| 4,578,401 | 3/1986 | Keller et al. | 514/49 |
| 4,668,513 | 5/1987 | Reichert | 424/94 |
| 4,758,427 | 7/1988 | Leeson | 514/293 |
| 5,179,122 | 1/1993 | Greene et al. | 514/458 |
| 5,198,432 | 3/1993 | Fariss | 514/182 |
| 5,223,268 | 6/1993 | Stetsko | 424/490 |
| 5,234,695 | 8/1993 | Hobbs et al. | 424/489 |
| 5,430,021 | 7/1995 | Rudnic et al. | 514/14 |
| 5,491,154 | 2/1996 | Ciceri et al | 514/356 |
| 5,558,876 | 9/1996 | Desai et al. | 424/427 |
| 5,583,105 | 12/1996 | Kovacs et al. | 514/11 |
| 5,696,101 | 12/1997 | Wu et al. | 514/57 |
| 5,798,333 | 8/1998 | Sherman | 514/11 |

OTHER PUBLICATIONS

Adams, M.W. D–Alpha Tocopheryl Polyehtylene Glycol 100 Succinate (Eastman Vitamin E TPGS) as an Emulsifier and Bioenhancer for Drugs and Lipophilic Compounds. Congr. Int. Technol. Pharm., 6th (1992), Vol. 4, pp.254–262. Assoc. Pharm. Galenique Ind., Chatenay Malabry, Fr..

Wu et al. Characterization of D–Alpha Tocopheryl Polyethylene Glycol–100 Duccinate for Applications as an Absorption Enhancer. Pharmaceutical Research, 11(10), S–149. 10/1994. Abstract.

*Primary Examiner*—Robert H. Harrison
*Attorney, Agent, or Firm*—Pennie & Edmonds LLP

[57] ABSTRACT

Lipophilic active ingredients are co-melted with tocopherol polyethyleneglycol succinate (TPGS) and a dispersion adjuvant to obtain solid dry coprecipitate compositions suitable as an oral dosage form. The solid TPGS coprecipitates of lipophilic active ingredients show improved drug release in vitro and enhanced oral bioavailability in vivo.

22 Claims, 6 Drawing Sheets

SOLID COPRECIPITATES FOR ENHANCED BIOAVAILABILITY OF LIPOPHILIC SUBSTANCES

FIELD OF THE INVENTION

The present invention concerns compositions comprising solid coprecipitates for improved oral delivery and enhanced bioavailability of lipophilic substances, and to methods for the preparation and use of these compositions. More particularly, these compositions include tocopherol polyethyleneglycol succinate powdered coprecipitates of lipophilic substances.

BACKGROUND OF THE INVENTION

Lipophilic substances possessing low water solubility often have poor oral bioavailability. These substances, being hydrophobic by nature, show wetting difficulties and poor dissolution. These properties obviously represent a rate-limiting step in their absorption from solid oral dosage forms and, in turn, cause a subsequent reduction in their bioavailability.

To address the foregoing issue, these lipophilic substances are usually administered in the form of liquid preparations dissolved in edible oils or formulated in oil-in-water emulsions or microemulsion. Even in these formulations, however, the oral bioavailability of many of them is still very low. Thus, even today, there remains an unresolved need for safe and useful formulations that provide enhanced oral bioavailability for such substances.

Cannabinoids are one example of a family of lipophilic substances with very poor water solubility. Cannabinoids such as $\Delta^1$-tetrahydrocannabinol ($\Delta^1$-THC), $\Delta^6$-tetrahydrocannabinol ($\Delta^6$-THC), $\Delta^9$-tetrahydrocannabinol ($\Delta^9$-THC), cannabinol, cannabidiol, and their metabolites, are highly hydrophobic lipid soluble compounds and can be dissolved in aqueous solutions only in the range of a few micrograms/ml or less, depending upon the conditions (Garret and Hunt, J. Pharm. Sci., 63:1056–1064,1974).

In general, the systemic availability of cannabinoids after oral administration is low and mean estimates of the human bioavailability of tetrahydrocannabinol (THC) following oral ingestion range from 6 to 12% depending on the vehicle used. For example, the maximal plasma levels after oral dosing of 20 mg THC in a sesame oil formulation were around 10 ng/ml (Wall et al., Clin. Pharmacol. Ther. 34:352–363, 1983).

Dexanabinol (also denoted HU-211), is disclosed in U.S. Pat. Nos. 4,876,276 and 5,521,215, as a synthetic non-psychoactive cannabinoid with novel neuroprotective activity in the multiple-action treatment of brain damage associated with stroke, head trauma, and cardiac arrest. The chemical structure of dexanabinol, (+)-(3S, 4S)-7-hydroxy-$\Delta^6$-tetra hydrocannabinol-1,1-dimetylheptyl, is shown in Scheme 1.

Scheme 1

Dexanabinol is a very lipophilic compound which is practically insoluble in water (less than 50 µg/ml) and, like other lipophilic drugs, exhibits poor oral bioavailability.

Coenzyme Q10, chemically named 2,3-dimethoxy-5-methyl-6-decaprenyl-1,4-benzoquinone and also known by the names Ubiquinone or Vitamin K, is classified as a fat-soluble quinone, a naturally occurring enzyme. It has been identified as an essential component of the mitochondrial respiratory chain, and, thus, a necessary part of a cell's energy production. More particularly, it constitutes a redox-link between flavoproteins and cytochromes and acts as an electron shuttle controlling the efficiency of oxidative phosphorylation. It is a very lipophilic compound and practically insoluble in water due to its long side chain of 10 isoprenoid units.

CoQ10 has been previously identified as a natural antioxidant with potential use as a dietary supplement to protect against age-related degeneration and as an adjuvant vitamin to prevent or treat many disease states.

Supplementary Coenzyme Q10 has reportedly shown beneficial influences in a variety of conditions or diseases, including: periodontal disease, certain blood circulation diseases, impaired memory, fatigue, irregular heartbeat, high blood pressure, immune system impairment, and the aging process.

The recommended daily allowance for coenzyme Q10 has not been determined. Most experts agree, however, that the daily requirement lies somewhere between 30 and 60 milligrams. When treating illnesses, dosages of 100 to 300 milligrams are commonly used.

The oral bioavailability of CoQ10 is related to the dissolution rate of the formulation (Kishi et al., Metabolism of exogenous coenzyme Q10 in vivo and the bioavailability of coenzyme Q10 preparations in Japan, in: K. Folkers, and Y. Yamamura, eds., Biomedical and Clinical Aspects of Coenzyme Q10, Vol. 4, Elsevier, Amsterdam, 1984, pp. 131–142).

Given CoQ10's poor solubility in water, the ability to formulate this substance in a suitable form affording convenient and efficient oral bioavailability is a desired goal. The art has attempted to address the problem by disclosing formulations of Coenzyme Q10 using lipids, in the form of emulsions, liposomes, microparticles and nanoparticles, have previously been disclosed. These known lipid formulations have comprised particles dispersed in an aqueous medium, and are suitable for various routes of administration, including primarily intravenous administration, as disclosed in: WO 95/05164, which discloses microparticles and nanoparticles in aqueous suspension; U.S. Pat. No. 4,824,669, which discloses fatty emulsions; U.S. Pat. No. 4,636,381, which discloses liposomes; and U.S. Pat. No. 4,483,873, which discloses aqueous dispersions or solutions.

The neurohormone melatonin is synthesized in the pineal gland with a nocturnal circadian rhythm. Sleep disorders, seasonal depression, mood disorders, migraine, and jet lag are some of the disorders that have been correlated to a disruption of normal, physiological melatonin secretion. There are reports on the beneficial effect of exogenous melatonin administration to reestablish the synchronization of circadian rhythm. However, these studies have shown large variations in oral melatonin absorption, as well as highlighted the inconvenience of employing a continuous intravenous delivery system. Therefore, an oral formulation of melatonin with good bioavailability is needed. A melatonin buccal mucoadhesive sustained release delivery patch, mimicking endogenous secretion, has already been shown as one alternative means for delivering melatonin (Benes et al., Proceed. Intl. Symp. Control. Rel. Bioact. Mater., 21:551–552, 1994).

Additional examples of lipophilic drugs with very poor water solubility and low oral bioavailability which could benefit from oral dosage forms are the antifungal agent amphotericin B, the anticancer drug etoposide, as well as tamoxifen and its analogs.

Water-dispersible vitamin preparations were disclosed in U.S. Pat. No. 3,102,078, wherein the vitamin E derivative tocopherol polyethyleneglycol succinate (TPGS) was shown to have useful properties as a solubilizing agent. Oily compositions of anti-tumor drugs utilizing TPGS as a solubilizing adjuvant have also been disclosed for instance in U.S. Pat. No. 4,578,391. Further uses of TPGS as a surface active substance (U.S. Pat. No. 4,668,513), as a cryoprotectant (U.S. Pat. No. 5,198,432) or to improve the bioavailability of vitamin E (U.S. Pat. Nos. 5,179,122 and 5,223,268) have also been disclosed. A powder formulation of water dispersible vitamin E compositions for use as a vitamin E supplement has also been disclosed in U.S. Pat. No. 5,234,695.

The structure of TPGS is shown in scheme 2

Scheme 2 where n represents the average number of —CH$_2$CH$_2$O— groups in the polyethylene glycol chain. For typical polyethylene glycols, n is from about 5.2 (PEG 200) to about 182.4 (PEG 8000). Thus, there remains a need for new formulati provide improved oral bioavailability of such compounds. The present invention provides such formulations.

SUMMARY OF THE INVENTION

This invention is directed to compositions comprising tocopherol polyethyleneglycol succinate (TPGS) solid coprecipitates useful for the oral delivery of lipophilic substances with low oral bioavailability, and to methods for preparing and using such compositions.

The solid coprecipitate compositions of the present invention include a lipophilic substance in an amount sufficient to provide a therapeutic effect when administered to a mammal; tocopherol polyethyleneglycol succinate (TPGS) in an amount sufficient to increase the oral availability of the lipophilic substance; and a dispersion adjuvant in an amount sufficient to assist in dispersing the lipophilic substance in the succinate.

According to a preferred embodiment of the present invention, the solid TPGS coprecipitates of the present invention comprise a dispersion adjuvant selected from the group consisting of polyvinylpyrrolidone, a medium chain triglyceride, a long chain triglyceride, tocopherol acetate, and polyethyleneglycol.

According to a more preferred embodiment, the solid TPGS coprecipitates of the present invention, comprise polyvinylpyrrolidone (PVP) as the dispersion adjuvant.

According to a most preferred embodiment of the present invention, the solid TPGS coprecipitates of the present invention may advantageously further comprise a known free-flow imparting agent, such as fumed silica or the like. This embodiment provides powdered TPGS coprecipitates particularly useful in the preparation of solid dosage forms for oral administration.

Lipophilic substances incorporated in the powdered TPGS coprecipitates of the present invention have shown unexpectedly improved drug release in simulated gastric fluid in vitro and enhanced oral bioavailability in vivo.

The present invention further relates to methods for producing the powdered TPGS coprecipitate compositions, comprising:

co-melting TPGS and the lipophilic substance at 40°–60° C.;

adding a dispersion adjuvant to the melted mixture with agitation;

adding a fumed silica to the mixture with agitation; and drying the resultant mixture at 100° C. to get a dry coprecipitate.

The dispersion adjuvant used in accordance with this method may be added as an aqueous solution, an organic cosolvent solution, or an oil.

According to yet another embodiment, the solid TPGS coprecipitate compositions according to the present invention may be prepared by freeze-drying the TPGS/lipophilic substance/dispersing adjuvant mixture.

According to yet another embodiment, the solid TPGS coprecipitates compositions according to the present invention may be prepared by spray-drying the TPGS/lipophilic substance/dispersing adjuvant mixture.

According to a more preferred embodiment, the TPGS/lipophilic substance/dispersing adjuvant coprecipitate formulations can be spray dried or freeze-dried to obtain dry powdered compositions, suitable for the preparation of solid-dosage forms such as hard gelatin capsules or tablets.

According to a still more preferred embodiment, these solid dosage TPGS coprecipitate compositions are advantageous for the oral delivery of Coenzyme Q10 as a dietary nutrient supplement, melatonin, dexanabinol, amphotericin B, etoposide, tamoxifen quaternary amine analogs, or for any appropriate lipophilic substance.

DETAILED DESCRIPTION OF THE INVENTION

This invention is directed to compositions comprising dry tocopherol polyethyleneglycol succinate solid coprecipitates useful for the oral delivery of lipophilic substances, and to methods for preparing and using such compositions.

Examples of lipophilic substances that exhibit poor oral bioavailability include lipophilic drugs, vitamins, and hormones. These include steroids, steroid antagonists, non-steroidal anti-inflammatory agents, antifungal agents, antibacterial agents, antiviral agents, anticancer agents, antihypertensives, anti-oxidants, anti-epileptic agents and antidepressants among many others. Additional examples of lipophilic drugs with very poor water solubility and low oral bioavailability which could benefit from oral dosage forms are the neurohormone melatonin, the antifungal agent amphotericin B, the anticancer drug etoposide, as well as tamoxifen and its analogs. More specific compounds include cannabinoids, as exemplified by dexanabinol, and vitamins, enzymes or coenzymes, as exemplified by CoQ10. Preferred lipophilic substances are those which have a water solubility of <200 $\mu$g/ml in water at room temperature (25° C.), and more preferably <50 $\mu$g/ml.

The present invention discloses a novel way to increase the oral bioavailability of a lipophilic substance. More particularly, the invention relates to solid coprecipitates comprising the lipophilic substance, a surfactant vehicle having a melting point close to human body temperature, and at least one dispersion agent/adjuvant.

After mixing with body fluids, such as gastric fluid, these compositions undergo quick dissolution with resultant micelle formation or emulsification. A good example of a surfactant vehicle (which can quickly disperse drug coprecipitates) is alpha-tocopherol polyethylene glycol succinate (TPGS), which was first disclosed in U.S. Pat. No. 3,102,078. TPGS is an amphipathic molecule, prepared by the esterification of a hydrophilic polyethylene glycol molecule (usually with a mean molecular weight 1000, and about 20–25 ethylene oxide chains) with the carboxylic group of hydrophobic d-alpha-tocopherol hemisuccinate (acid). TPGS is a water soluble compound (to 20% w/v) and forms micellar solutions with a critical micelle concentration (CMC) of 0.4–0.6 mM (about 0.075%). The hydrophilic-lipophilic balance (HLB) of TPGS is about 15–19. The amphipathic nature of TPGS, high HLB and water solubility, and low CMC make the molecule an excellent emulsifying agent for lipophilic substances. The emulsification and subsequent increase in surface area of the lipophilic substance results in increased gastrointestinal drug absorption and bioavailability.

Toxicological studies have shown that TPGS is safe for ingestion by humans as a dietary or nutritional supplement. In conclusion, TPGS can be safely used as a surfactant and a bioenhancer for lipophilic substances of limited absorption in gastrointestinal region. Moreover, the antioxidative properties of TPGS improve the stability of TPGS containing formulations.

According to the present invention, it now is disclosed that solid TPGS coprecipitate formulations self-emulsify when dispersed in a aqueous medium, like gastric fluid, forming very small drug mixed-micelles. Lipophilic substances loaded in TPGS solid coprecipitate formulations will be absorbed more easily by the gastrointestinal tract enhancing its oral bioavailability.

The solid TPGS coprecipitates of the present invention are composed of three essential ingredients: a lipophilic substance with low water solubility, tocopherol polyethyleneglycol succinate, and at least one dispersion adjuvant.

According to a more preferred embodiment of the present invention, the solid TPGS coprecipitates of the present invention, may advantageously further comprise a free-flowing imparting agent, such as fumed silica (Cab-O-Sil, Cabot Corp., USA).

Lipophilic substances incorporated in the solid TPGS coprecipitates of the present invention have shown unexpectedly improved in vitro drug release in simulated gastric fluid and enhanced oral bioavailability.

The lipophilic substance content in the solid TPGS coprecipitates of the present invention may range from about 0.01–50% of the total solid weight of the composition, more preferably in the range of about 5–30% of the total solid weight of the composition, and still more preferably about 10–20% of the total solid weight of the composition.

The content of TPGS in the final coprecipitate formulations of the present invention is in the range of about 5–65% of the total solid weight of the composition, more preferably in the range of about 10–60% of the total solid weight of the composition, and still more preferably in the range of about 10–50% of the total solid weight of the composition.

The content of dispersion adjuvant in the final coprecipitate formulations of the present invention is in the range of about 5–75% of the total solid weight of the composition, more preferably in the range of about 10–40% of the total solid weight of the composition, and still more preferably in the range of about 10–30% of the total solid weight of the composition. This dispersion adjuvant is included to facilitate the homogeneous dispersion of the lipophilic substance in the mixture.

According to a preferred embodiment of the present invention, the solid TPGS coprecipitates of the present invention comprise a dispersion adjuvant selected from the group consisting of polyvinylpyrrolidone (PVP); a medium chain triglyceride or MCT oil; a long chain triglyceride or LCT oil; tocopherol acetate; polyethyleneglycol; or other adjuvant substance that can improve the dissolution of the lipophilic substance into the mixture or to help the lipophilic substance disperse homogeneously in the TPGS. Specific examples of such dispersion adjuvants include: Povidone (ISP Technologies, USA); Kollidon 12 PF (BASF, Germany); Miglyol 812 (Hulls, Germany); LCT oil (Croda); and Carbowax 1450 (Union Carbide, USA).

The solid TPGS coprecipitates of the present invention may further comprise any suitable nontoxic carrier or diluent powder known in the art to serve as a free-flow imparting agent. Common examples of such additives are silicon dioxide, starch, lactose, sucrose, sorbitol, talc, stearic acid, magnesium stearate, and dicalcium phosphate. When the compound is formulated into a tablet or pill, the tablet or pill can be coated or otherwise compounded with pharmaceutically acceptable materials known in the art to provide a dosage form affording prolonged action or sustained release. The solid TPGS coprecipitates may also be prepared in gelatin capsules.

According to a preferred embodiment, solid TPGS coprecipitates are further mixed with fumed silica, such as CAB-O-SIL® (Cabot Corp., IL., U.S.), which is a powdery material with extremely small particle size and enormous surface area.

Fumed silica can act as a dry lubricant, promoting the free flow of the powdery mixture and preventing the mixture from caking or lumping. The free-flow, anti-caking and anti-clogging characteristics which are imparted to powders, granules and pellets by the addition of small amounts of fumed silica are the result of several actions. For example, the submicroscopic size of the silica aggregates permits them to move easily between the larger particles of the other dry ingredients, and in most cases fumed silica probably forms a coating on the powder particles. The fumed silica layer also decreases bulk tensile strength and shear strength, while neutralizing the electrostatic charge on the particles.

After blending with the other powders, fumed silica adsorbs some or all the moisture which may be present in or on the product particles. The fumed silica aggregates prevent other particles from contacting each other to form the nuclei that would otherwise lead to the formation of larger lumps and cakes. This spacing and lubricating action helps to keep materials moving through the apertures of process equipment valves, spray heads, storage bin openings, bag and drum spouts, and aerosol nozzle orifices.

Most powdered materials can be kept free flowing by adding a concentration of fumed silica in the final product range of about 0.5–25% (total solid weight). The optimum concentration can be determined by working up or down in small steps. The more preferred weight percent of fumed silica in the final product will be in the range of about 1–20% (total solid weight). Even powders which have already become caked can usually be rendered free flowing by blending them with fumed silica (about 2% of the total solid weight, or less).

Products which cannot be processed beyond a sticky or tacky powder can be made free flowing by adding the proper level of fumed silica as a final finishing step. Fumed silica can also be used to promote free flow in spray-dried or freeze-dried products.

In some cases it can be introduced into the original emulsion, suspension or solution, or blended in later. Fumed silica has also been used to coat powdered and pelletized products to prevent them from caking later.

The content of silicon dioxide in the final solid TPGS coprecipitates is commonly in the range of about 5–20% of the total solid weight of the solid coprecipitate, and more preferably in the range of about 10–20% of the total solid weight of the solid coprecipitate.

The preparation of solid TPGS powdered coprecipitates of lipophilic substances of the present invention may be prepared by different methods as described in the following non-limiting examples.

EXAMPLES

Example 1

Preparation of tocopherol polyethyleneglycol succinate/polyvinylpyrrolidone powdered coprecipitates of Dexanabinol by freeze-drying This example illustrates the preparation of tocopherol polyethyleneglycol succinate/polyvinylpyrrolidone (TPGS/PVP) powdered coprecipitates of Dexanabinol by freeze-drying. The final weight/weight % composition of the different formulations prepared were as described in Table 1.

TABLE 1

Weight/weight % composition of TPGS/PVP/Dexanabinol coprecipitates

| Formulation Code and Ingredients | AY-91-169-6 | AY-91-175-2 | AY-91-175-2 | AY-91-175-10 | AY-91-175-3 | AY-91-175-4 |
|---|---|---|---|---|---|---|
| TPGS | 54 | 50 | 40 | 50 | 30 | 40 |
| Dexanabinol | 6 | 10 | 20 | 20 | 30 | 30 |
| PVP | 26 | 26 | 26 | 16 | 26 | 16 |
| Cab-O-Sil | 14 | 14 | 14 | 14 | 14 | 14 |

TPGS (Eastman-Kodak Co., USA) was comelted with PVP (Kollidon PF 12, BASF, Germany, added from a 10% solution in water) at 40°–60° C. in a water bath. Dexanabinol was added to the melted materials and the mixtures were gently agitated for several minutes. Cab-O-Sil (Cabot CORP., USA, added from a 5% solution in water) was added and the mixtures were agitated again for several minutes. After cooling to room temperature, TPGS/PVP/dexanabinol coprecipitates were formed. The coprecipitates were freeze-dried overnight using a Christ beta lyophilize (Germany). Powdered free-flowing coprecipitates quickly dispersible in water were obtained.

TPGS/PVP/dexanabinol coprecipitates containing additionally tocopherol acetate and Miglyol 812 as described in Table 2 were also prepared by freeze-drying using the same method, which resulted in the formation of powdered free-flowing coprecipitates quickly dispersible in water.

TABLE 2

Weight/weight % composition of TPGS/PVP/Dexanabinol coprecipitates containing Miglyol and tocopherol acetate.

| Formulation Code and Ingredients | AY-91-168-5 | AY-91-175-5 | AY-91-175-6 | AY-91-175-7 | AY-91-175-9 | AY-91-175-8 | AY-91-165-9 | AY-91-155 |
|---|---|---|---|---|---|---|---|---|
| TPGS | 13.4 | 13.4 | 13.4 | 13.4 | 13.4 | 13.4 | 25 | 23 |
| Tocopherol acetate | 20.3 | 15.3 | 10.3 | 20.3 | 20.3 | 8.3 | 37.5 | 34 |
| Miglyol 812 | 20.3 | 15.3 | 20.3 | 10.3 | 20.3 | 8.3 | 37.5 | 34 |
| Dexanabinol | 6 | 16 | 16 | 16 | 16 | 30 | — | 9 |
| PVP | 26 | 26 | 26 | 26 | 16 | 26 | — | — |
| Cab-O-Sil | 14 | 14 | 14 | 14 | 14 | 14 | — | — |

The obtained powdered coprecipitates were filled in hard gelatin capsules (No. 1) for in vitro release experiments in simulated gastric fluids and for oral bioavailability studies in rats (minicapsules, Torpac, N.J., USA).

Example 2

Preparation of TPGS/PVP powdered coprecipitates of Dexanabinol by spray-drying.

This example illustrates the preparation of a TPGS/PVP powdered coprecipitate of Dexanabinol by spray-drying. The final weight/weight % composition of the formulation prepared is described in Table 3:

TABLE 3

Weight/weight % composition of TPGS/PVP/Dexanabinol coprecipitate formulation prepared by spray-drying

| Formulatin Code and Ingredients | AY-91-175-3 |
|---|---|
| TPGS | 30 |
| Dexanabinol | 30 |
| PVP | 26 |
| Cab-O-Sil | 14 |

TPGS (249 mg) was melted in a water bath at 50° C. Dexanabinol (249 mg) were then added to the melted TPGS and the mixture was shaken for several minutes at 50° C. PVP (2.2 ml of a 10% solution in water) was added to the comelted mixture of TPGS/Dexanabinol TPGS and the mixture was shaken again for several minutes. Finally, Cab-O-Sil (2.3 ml of a 5% solution in water) was added and the formulation was shaken again for 1 hr at 50° C.

The resultant formulation was spray-dried using a Yamato Pulvis GA32 Mini spray-dryer. The drying conditions were: flow rate 7 ml/min, inlet temperature 130° C., outlet temperature 80° C., and drying air flow 0.45 m³/min. A homogeneous and quickly water-dispersible dry powder of the TPGS/PVP/Dexanabinol coprecipitate was obtained.

Example 3
In vitro release of Dexanabinol from solid lipid TPGS coprecipitates in simulated gastric fluid In vitro drug release of Dexanabinol from solid TPGS lipid coprecipitates was determined by placing a hard gelatin capsule No. 1 containing the formulation in 50 ml of simulated gastric fluid (150 mM NaCl, pH 1.2, 37° C., containing 1% Tween 80 as sink). Gentle stirring was provided by a magnetic bar. Samples were drawn from the release medium at prefixed time intervals and filtered through a 2.7 µm PTFE filter (Whatman).

Dexanabinol was determined by HPLC using a Kontron instrument equipped with pump, UV detector, and autosampler. A summary of the typical chromatographic conditions of the method is provided below:

Column: Merck 50980 supersphere 100RP-18, 75×4 mm, 4 µm.

Mobile Phase: 30% phosphate buffer (0.01M $KH_2PO_4$, pH 3.0): 70% acetonitrile (v/v). Flow rate: 1 ml/min. Detector wavelength: 280 nm. Injection volume: 20 µl. Column temperature: ambient. Retention time: about 5.8 min. Run time: about 9 min.

Figure 1:
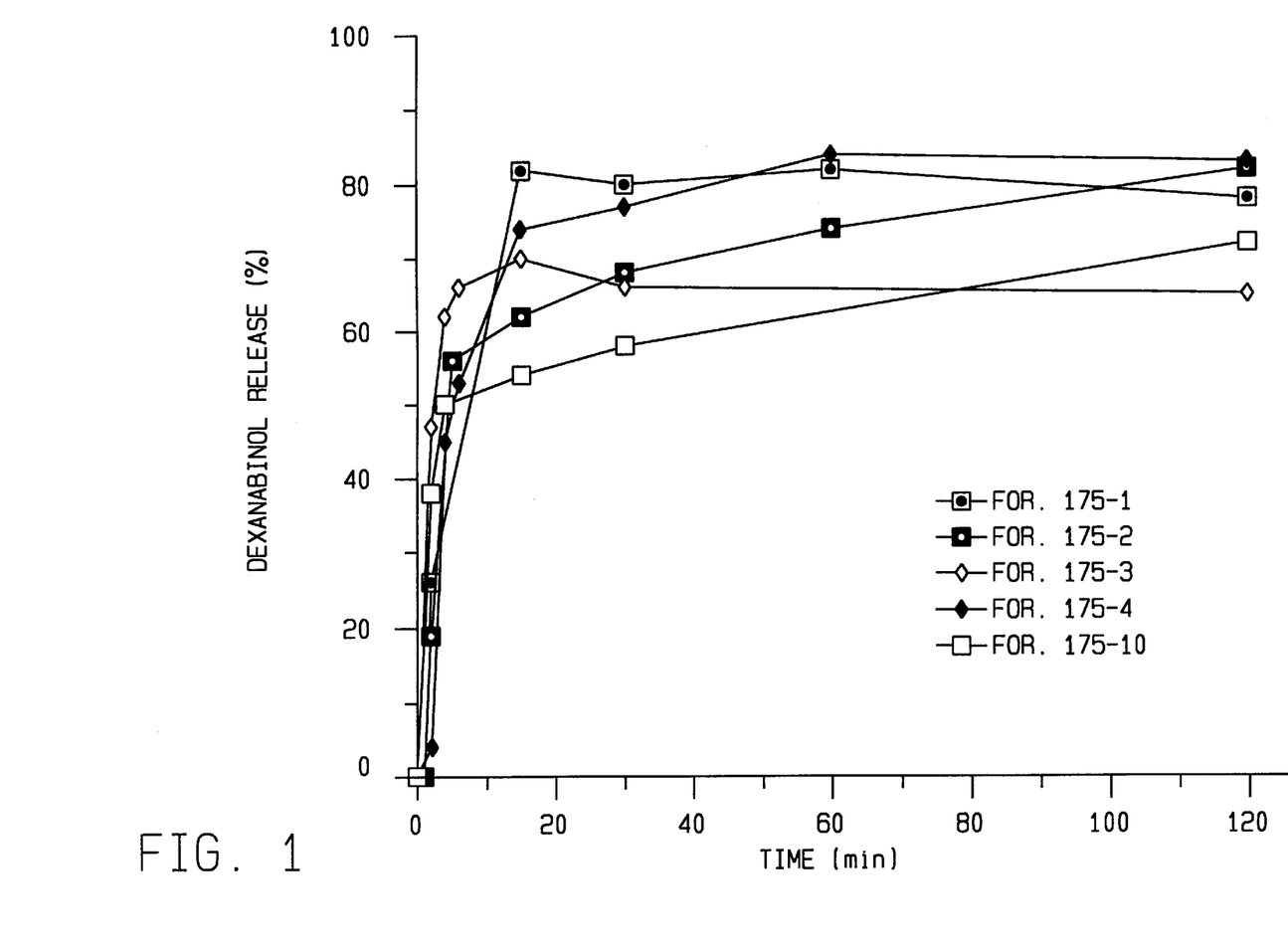
FIG. 1 shows the in vitro release patterns of Dexanabinol in simulated gastric fluid from powdered TPGS/PVP solid lipid coprecipitate compositions containing about 2.5 mg drug prepared as described in Example 1 (Table 1) and packed in hard gelatin capsules.

FIG. 1 shows the in vitro release data for TPGS/PVP/Dexanabinol coprecipitate formulations in simulated gastric fluid. Depending on the specific composition of the formulation, very good Dexanabinol release (from 60–95%) was obtained—mainly during the initial 10–20 min.

Example 4
Enhanced oral bioavailability of Dexanabinol in solid TPGS coprecipitate formulations The solid TPGS powdered coprecipitates were filled in hard gelatin minicapsules (Torpac, N.J., USA) and tested for their oral bioavailability in rats. Male Sprague-Dawley rats (220–260 g, n=4) were administered orally with Dexanabinol formulated either as TPGS coprecipitates as described in Example 1 (Tables 1, 2, and 3) and filled in hard gelatin minicapsules (Torpac, N.J., USA) or in a MCT oil solution at 10, 25, and 50 mg/kg doses. Blood samples were collected at 0, 0.5, 1.0, 2.0, 3.0, 5.0, 8.0, and 24 hour time intervals. The samples were centrifuged at 10,000 rpm for 5 min and the plasma was separated and stored frozen at −20° C. until plasma Dexanabinol levels were analyzed. Determination of Dexanabinol in the plasma was performed by HPLC. The chromatographic conditions were as described in Example 3. Plasma samples stored at −20° C. were defrosted and diluted 1:4 as follows: 150 µl plasma sample was transferred into a 1.8 ml Eppendorf tube and 150 µl of acetonitrile were added. The sample was vortexed and centrifuged in a microfuge for 10 minutes at 10,000 rpm. The upper clear liquid was then transferred into an HPLC glass conical vial. A calibration curve was used for calculating Dexanabinol plasma levels. Corrections of sample peak areas were done by subtracting the of average value of the peak area obtained for samples at zero time (blank plasma).

Figure 2:
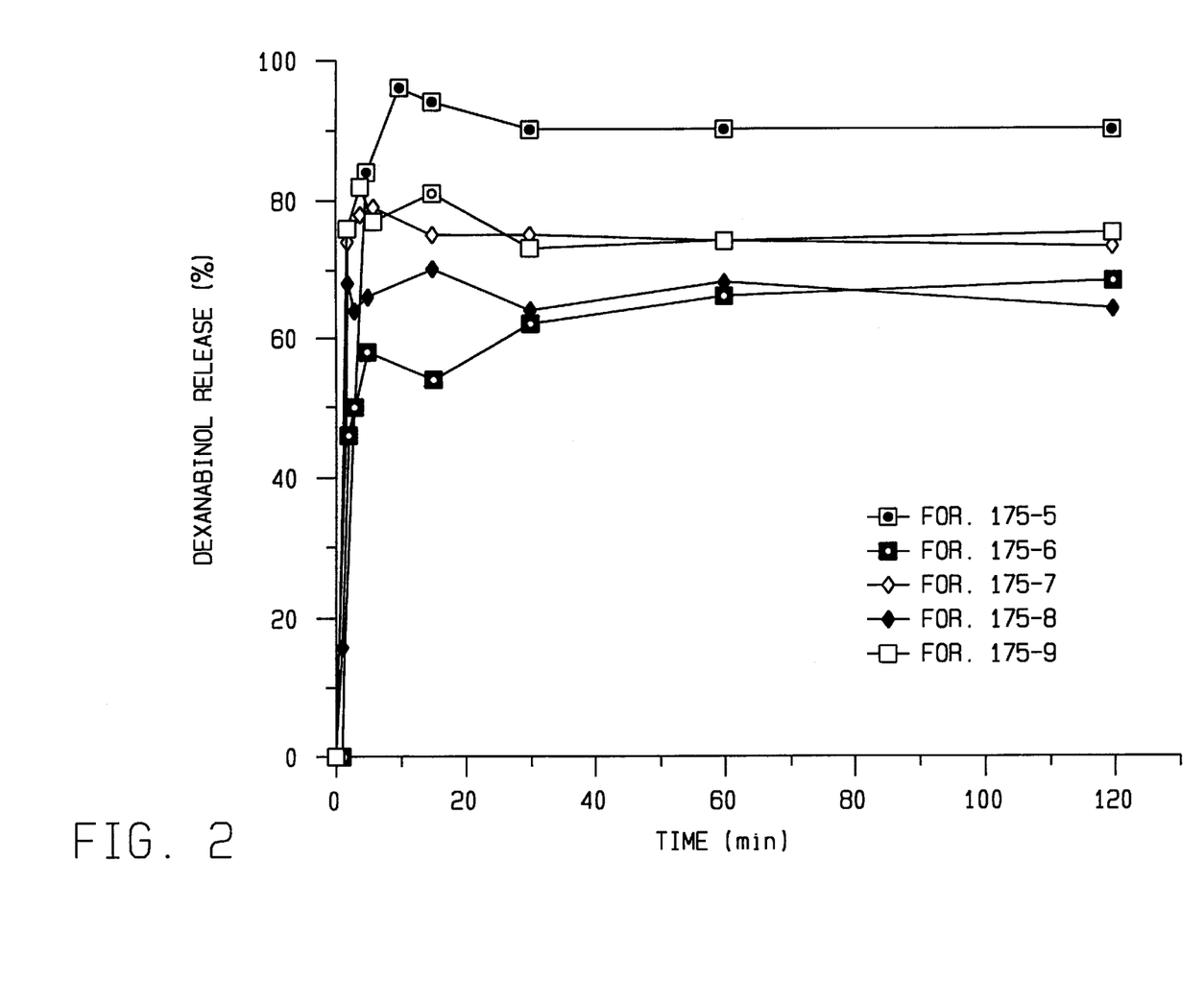
FIG. 2 shows the in vitro release patterns of Dexanabinol in simulated gastric fluid from powdered TPGS/PVP/Miglyol solid lipid coprecipitate compositions containing about 2.5 mg drug prepared as described in Example 1 (Table 2) and packed in hard gelatin capsules.

FIG. 2 shows the oral pharmacokinetics of Dexanabinol administered to rats (n=5) at a 50 mg/kg dose as a solid TPGS lipid coprecipitate (Formulation AY-91-155 prepared as described in Example 1, Table 2) compared to a solution of the drug in MCT oil (Miglyol 812). A two fold increase in Dexanabinol plasma levels was obtained with the coprecipitate formulation compared to the oil solution, demonstrating enhanced oral absorption of Dexanabinol from the solid TPGS coprecipitate formulation. This data indicates the good water dispersibility of the formulation, which, in turn, probably facilitates the uptake of the drug from the gastrointestinal tract.

Figure 3:
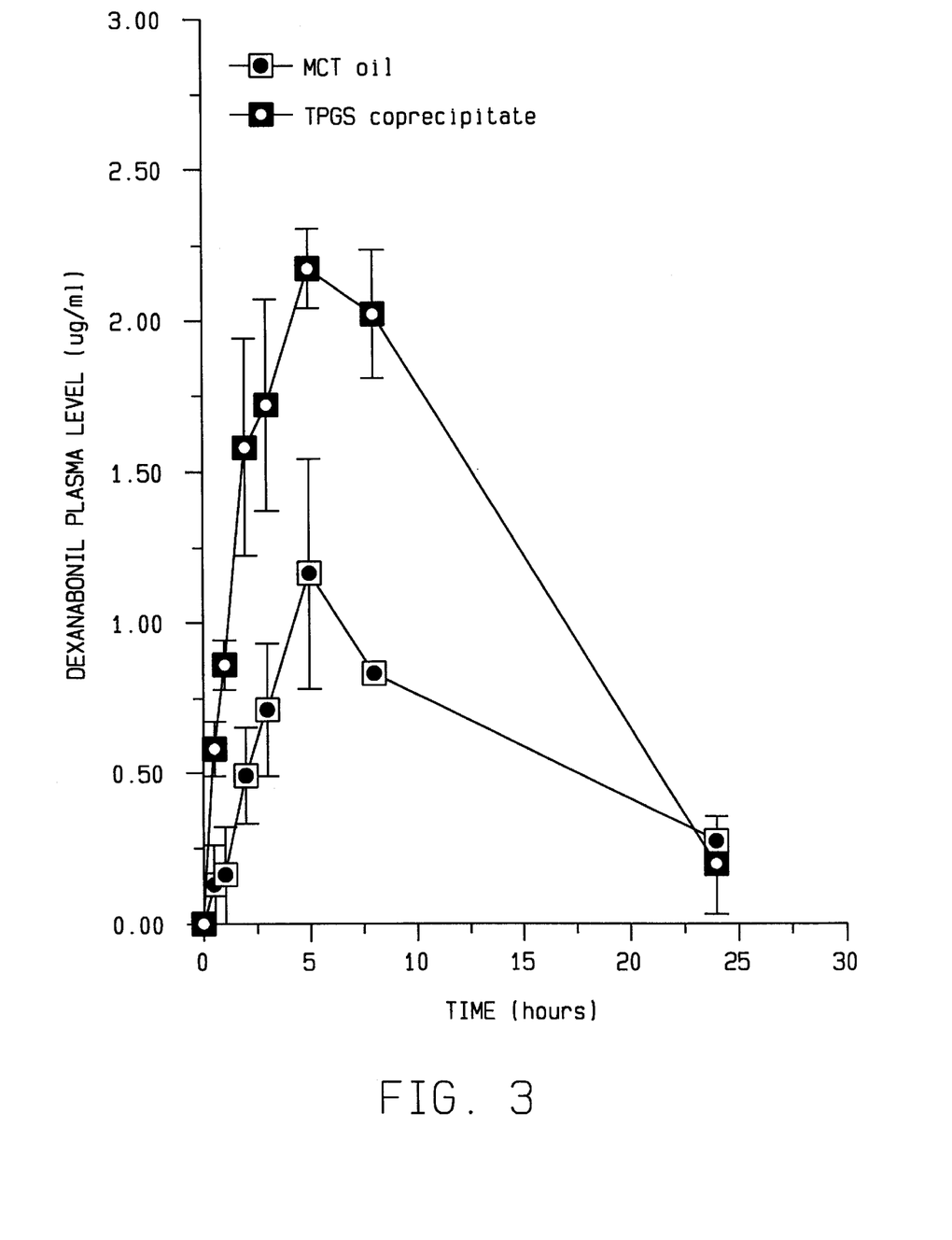
FIG. 3 shows the Dexanabinol rat plasma levels after oral administration (50 mg/kg drug, n=5) of a solid TPGS lipid coprecipitate composition (Formulation AY-91-155, Example 1, Table 2) compared to a MCT oil solution of the drug.

FIG. 3 shows the rat oral pharmacokinetics of Dexanabinol from TPGS solid lipid coprecipitate formulation (Formulation AY-91-155 prepared as described in Example 1, Table 2) at three different doses. A maximal drug concentration ($C_{max}$) was obtained after 5 hours ($t_{max}$) for all three doses tested, 10, 25, and 50 mg/kg.

Figure 4:
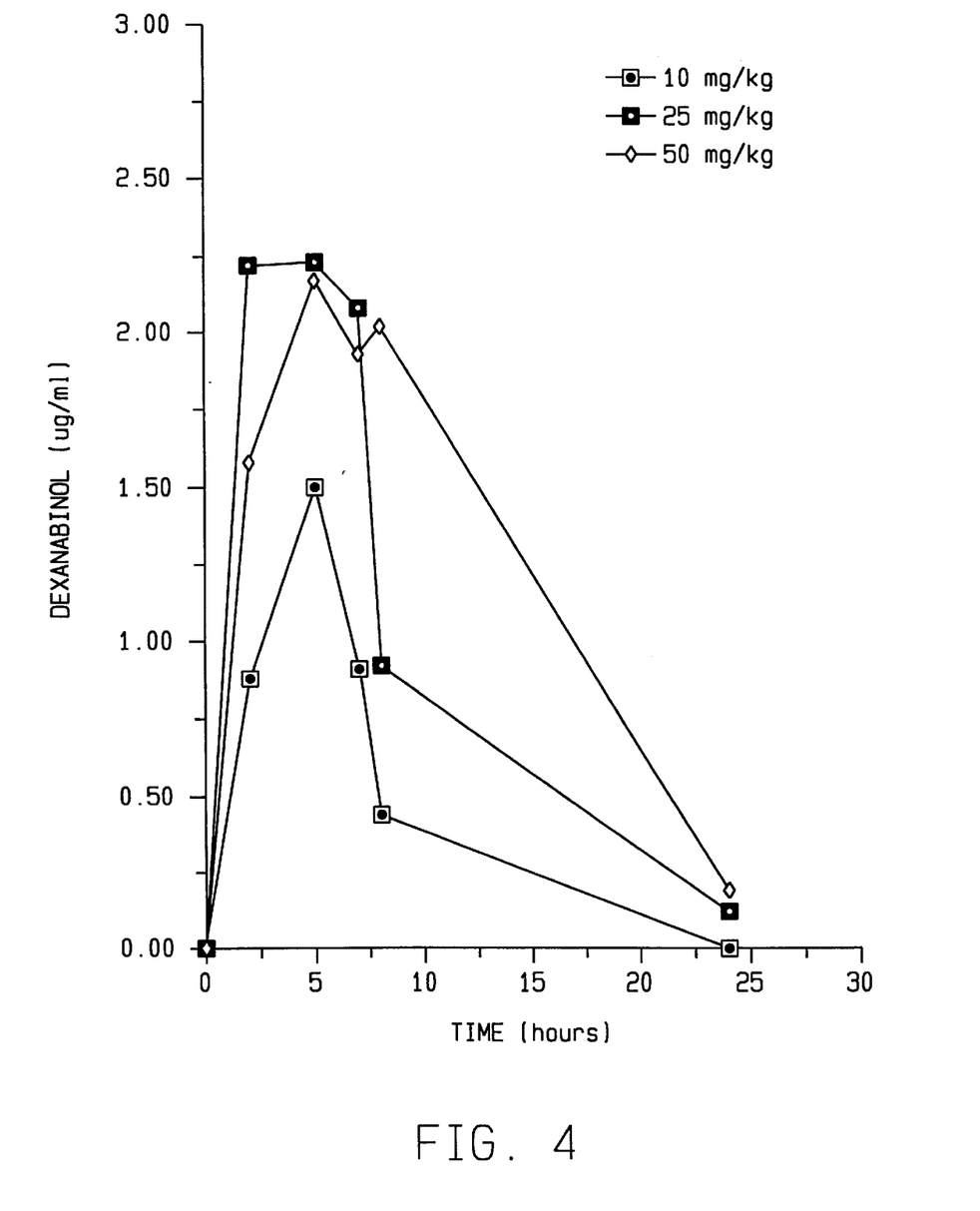
FIG. 4 shows the oral pharmacokinetics in rats of Dexanabinol formulated in a solid TPGS lipid coprecipitate (Formulation AY-91-155, Example 1, Table 2) at three different dosages.

FIG. 4 illustrates the oral pharmacokinetics of Dexanabinol administered to rats (n=5) at a 30 mg/kg dose as a powdered solid TPGS/PVP lipid coprecipitate in hard gelatin minicapsules (Formulation AY-175-3 prepared as described in Example 1, Table 1). The figure shows increased plasma levels of the drug and demonstrating the improved delivery and oral bioavailability of Dexanabinol.

Example 5
Preparation of solid TPGS lipid coprecipitates of Ubiquinone (coenzyme Q10)

This example illustrates the preparation of tocopherol polyethyleneglycol succinate coprecipitates of Coenzyme Q10. The final weight/weight % composition of the different formulations prepared is described in Table 4:

TABLE 4

Weight/weight % composition of TPGS/CoQ10 coprecipitates

| Formulation Code and Ingredients | 106-19B | 106-19C | 106-16A | 106-11C |
|---|---|---|---|---|
| TPGS | 20 | 21 | 47.1 | 47.5 |
| Coenzyme Q10 | 5 | 5 | 5.8 | 5 |
| MCT oil | 75 | — | — | — |
| LCT oil | — | 74 | — | — |

TABLE 4-continued

Weight/weight % composition of TPGS/CoQ10 coprecipitates

| Formulation Code and Ingredients | 106-19B | 106-19C | 106-16A | 106-11C |
|---|---|---|---|---|
| PVP | — | — | 47.1 | — |
| PEG 1450 | — | — | — | 47.5 |

Ubiquinone (Coenzyme Q10) was obtained from Global Marketing Associates, Inc. (San Francisco, Calif.). The polyethyleneglycol used was Carbowax PEG 1450 from Union Carbide (Conn., USA). The MCT oil (medium chain triglycerides) used was Miglyol 812 (Hulls, Germany). LCT oil (long chain triglycerides) was from Croda. TPGS/CoQ10 coprecipitates were prepared by heating together all the components at 50°–60° C. with subsequent cooling to room temperature. Compositions containing polyvinylpyrrolidone (PVP K-12) were prepared using 50% PVP solutions in absolute ethanol and drying the obtained mixture at 40°–45° C. for 4–6 hours. The obtained TPGS/CoQ10 coprecipitates showed quick water dispersibility with rapid release of the CoQ10.

Example 6
Preparation of TPGS/PVP powdered coprecipitates of Ubiquinone (coenzyme Q10) by freeze-drying This example illustrates the preparation of tocopherol polyethyleneglycol succinate powdered coprecipitates of Coenzyme Q10 by freeze-drying. The final weight/weight % composition of the different formulations prepared is described in Table 5:

TABLE 5

Weight/weight % composition of TPGS/PVP/CoQ10 powdered coprecipitates.

| Formulation Code and Ingredients | ED-107-157 | ED-107-155-1 | ED-107-155-B | AY-91-175-C |
|---|---|---|---|---|
| TPGS | 40 | 56 | 50 | 66 |
| Coenzyme Q10 | 9 | 13 | 11 | 15 |
| PVP | 41 | 15 | 25 | — |
| Cab-O-Sil | 10 | 16 | 14 | 19 |

TPGS (Eastman-Kodak Co., USA) was melted at 40°–60° C. in a water bath. Coenzyme Q10 was added to the melted TPGS and the mixtures were gently agitated for several minutes. PVP (Kollidon PF 12, BASF, Germany) was then added from a 30% solution in water and the mixtures were shaken at 40° C. for 1–2 hr. Cab-O-Sil (Cabot CORP., USA, added from a 5% solution in water) was added and the mixtures were agitated again for several minutes. After cooling to room temperature TPGS/PVP/CoQ10 coprecipitates were formed. The coprecipitates were freeze-dried overnight using a Christ beta lyophilizer (Germany). Powdered free-flowing coprecipitates quickly dispersible in water were obtained. They were packed in hard gelatin capsules for in vitro release studies.

Example 7
In vitro Release of Coenzyme Q10 from powdered TPGS/PVP coprecipitates in simulated gastric fluid In vitro drug release of CoQ10 from a powdered TPGS/PVP coprecipitate formulation and from a commercial product containing equivalent amounts of CoQ10 were determined by placing a hard gelatin capsule in 50 ml of simulated gastric fluid (150 mM NaCl, pH 1.2, 37° C.) containing 1% Tween 80 as sink. Gentle stirring was provided by a magnetic bar. Samples were drawn from the release medium at prefixed time intervals, filtered through a 2.7 $\mu$m Whatman GF filter and analyzed for CoQ10 concentration.

Figure 5:
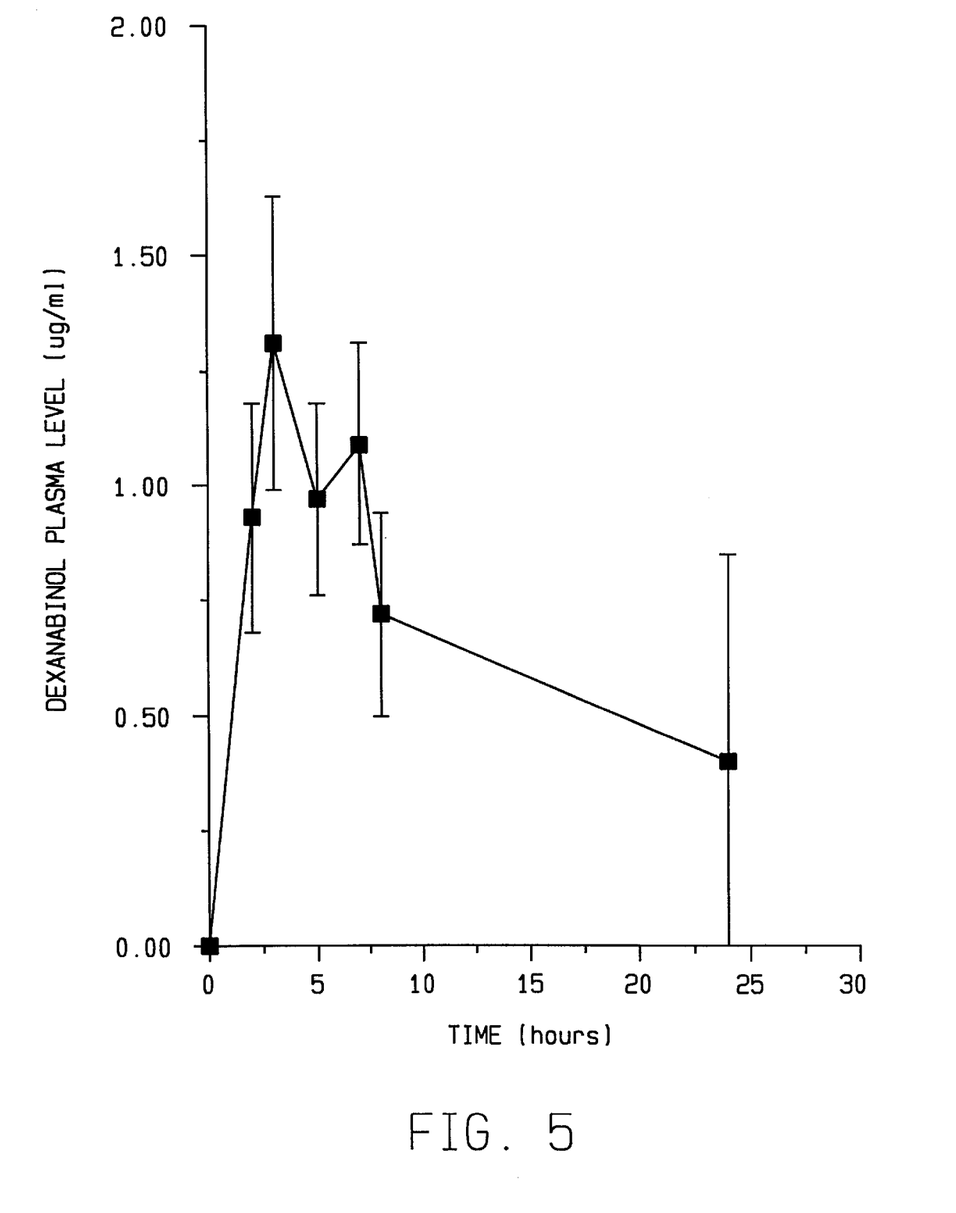
FIG. 5 shows the Dexanabinol rat plasma levels after oral administration (30 mg/kg drug, n=5) of a powdered solid TPGS lipid coprecipitate composition (Formulation AY-175-3) prepared as described in Example 1 (Table 1).
Figure 6:
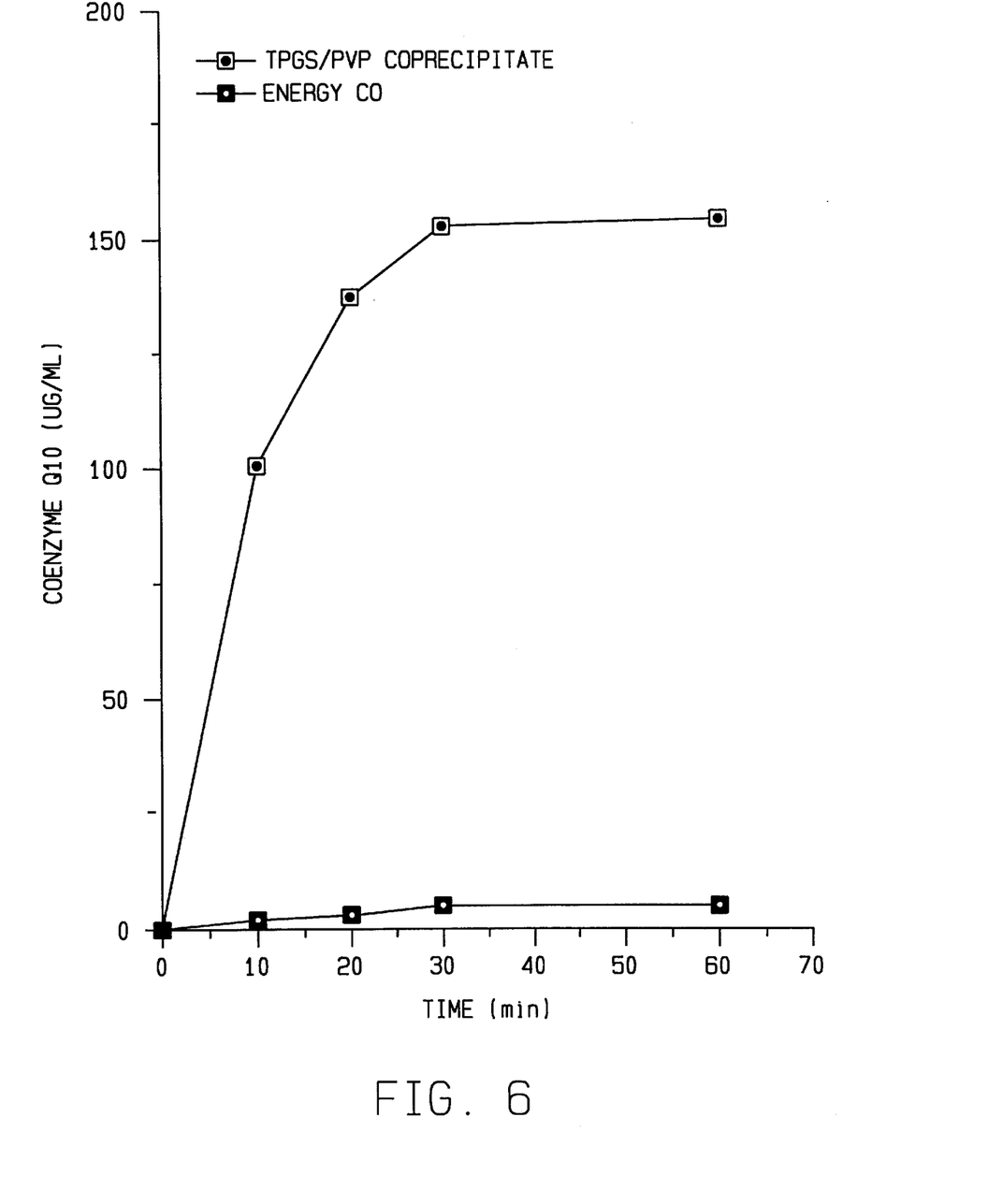
FIG. 6 shows the in vitro release of CoQ10 in simulated gastric fluid from commercial CoQ10 gelatin capsules and from a powdered solid TPGS/PVP lipid coprecipitate formulation (ED-107-157, Example 5, Table 5) packed in gelatin capsule.

FIG. 5 shows the in vitro release patterns of CoQ10 from a powdered TPGS/PVP coprecipitate formulation compared to a commercial product ENERGYCO® CoQ10 (Herbamed-Assutech Ltd., Rehovot, Israel) in simulated gastric fluid.

CoQ10 was determined in the commercial product, the powdered TPGS/PVP coprecipitate formulation, and in the release medium in vitro by extraction with Dole reagent (isopropanol:heptane:water, 45:36:17) by measuring the absorbance at 270 nm using a calibration curve. CoQ10 samples (0.5 ml) were added to 3.5 ml of Dole reagent and mixed thoroughly. The two phases were then allowed to separate for 10 min at room temperature. CoQ10 was extracted selectively in Dole heptane upper phase, which was transferred to a quartz cuvette for absorbance measurement.

The % release of CoQ10 from the marketed product was very low compared to a very quick and significant release from the powdered TPGS/PVP coprecipitate formulation. Each ENERGYCO® CoQ10 hard gelatin capsule contains 50 mg of CoQ10 mixed with rice powder. After capsule disruption in the simulated gastric fluid, big aggregates or clusters of CoQ10 and swelled rice powder were observed. These observations may explain the low CoQ10 dissolution into the release medium. Since particle size is a determinant factor in the rate and extent of drug absorption from the gastrointestinal tract, this result indicates low oral bioavailability of CoQ10 from the commercial product compared to powdered TPGS/PVP coprecipitate formulation of the present invention, which is quickly dispersible in the simulated gastric fluid.

Example 8
Preparation of TPGS/PVP powdered coprecipitate of Melatonin

TPGS (500 mg) was melted at 40°–60° C. in a water bath. Melatonin (100 mg, from Jansenn Chimica, Belgium) was added to the melted material and the mixture was agitated for several minutes. A small amount of absolute ethanol (up to 5%, v/v) was added in order to get an homogeneous mixture. PVP (Kollidon PF 12, 2.6 ml of a 10% solution in water) was then added and the mixture was agitated again for several minutes. Cab-O-Sil (2.8 ml of a 5% solution in water) was added and the mixture was agitated again for several minutes. The resultant TPGS/PVP/melatonin mixture was then freeze-dried overnight using a Christ beta lyophilizer (Germany). A powdered free-flowing TPGS/PVP/melatonin coprecipitate quickly dispersible in water was obtained.

Example 9
Preparation of TPGS/PVP powdered coprecipitate of Amphotericin B

TPGS (500 mg) was melted at 40°–60° C. in a water bath. Amphotericin B (100 mg, from Dumex, Denmark) was added to the melted material and the mixture was agitated for several minutes. A small amount of absolute ethanol (up to 5%, v/v) was added in order to get an homogeneous mixture. PVP (Kollidon PF 12, 2.6 ml of a 10% solution in water) was then added and the mixture was agitated again for several minutes. Cab-O-Sil (2.8 ml of a 5% solution in water) was added and the mixture was agitated again for several minutes. The resultant TPGS/PVP/Amphotericin B mixture was then freeze-dried overnight using a Christ beta lyophilizer (Germany). A powdered free-flowing TPGS/PVP/Amphotericin B coprecipitate quickly dispersible in water was obtained.

Example 10
Preparation of TPGS/PVP powdered coprecipitate of Tamoxifen methyiodide TPGS (500 mg) was melted at 40°–60° C. in a water bath. Tamoxifen methiodide (100 mg, from Pharmos Corp., FL., USA) was added to the melted material and the mixture was agitated for several minutes. A small amount of absolute ethanol (up to 5%, v/v) was added in order to get an homogeneous mixture. PVP (Kollidon PF 12, 2.6 ml of a 10% solution in water) was then added and the mixture was agitated again for several minutes. Cab-O-Sil (2.8 ml of a 5% solution in water) was added and the mixture was agitated again for several minutes. The resultant TPGS/PVP/Tamoxifen methiodide mixture was then freeze-dried overnight using a Christ beta lyophilizer (Germany). A powdered free-flowing TPGS/PVP/Tamoxifen methyliodide coprecipitate quickly dispersible in water was obtained.

Example 11
Preparation of TPGS/PVP powdered coprecipitate of Etoposide

TPGS (500 mg) was melted at 40°–60° C. in a water bath. Etoposide (100 mg, from Sigma, St. Louis, USA) was added to the melted material and the mixture was agitated for several minutes. A small amount of absolute ethanol (up to 5%, v/v) was added in order to get an homogeneous mixture. PVP (Kollidon PF 12, 2.6 ml of a 10% solution in water) was then added and the mixture was agitated again for several minutes. Cab-O-Sil (2.8 ml of a 5% solution in water) was added and the mixture was agitated again for several minutes. The resultant TPGS/PVP/Etoposide mixture was then freeze-dried overnight using a Christ beta lyophilizer (Germany). A powdered free-flowing TPGS/PVP/Etoposide coprecipitate quickly dispersible in water was obtained.

It will be appreciated by the artisan that many additional modifications or variations of these compositions are feasible. The scope of the invention is, therefore, not to be construed as limited to the foregoing examples, but is to be construed, at the very least, to be commensurate with the scope of the following claims.

What is claimed is:

1. A solid composition comprising: a lipophilic substance having a water solubility of less than 200 $\mu$q/mL at 25° C. in an amount sufficient to provide a therapeutic effect when administered to a mammal; about 5–65%, based on the total solid weight of the composition, of tocopherol polyethyleneglycol succinate (TPGS); and about 5–75%, based on the total solid weight of the composition, of a dispersion adjuvant, wherein the lipophilic substance and the dispersion adjuvant are different compounds.

2. The composition of claim 1 wherein the dispersion adjuvant is selected from the group consisting of a polyvinylpyrrolidone, a medium chain triglyceride, a long chain triglyceride, a polyethyleneglycol, and a tocopherol acetate.

3. The composition of claim 1 which further comprises a solid carrier or diluent.

4. The composition of claim 1, wherein the lipophilic substance has a solubility in water of less than 50 $\mu$g/mL at 25° C.

5. The composition of claim 1 wherein the lipophilic substance comprises about 0.01–50% of the total solid weight of the composition.

6. The composition of claim 1 wherein the dispersion adjuvant is polyvinylpyrrolidone.

7. The composition of claim 6 which further comprises a second dispersion adjuvant selected from the group consisting of an MCT oil, an LCT oil, polyethylene glycol, and tocopherol acetate.

8. The composition of claim 3, wherein the solid carrier or diluent comprises fumed silicon dioxide in the amount of about 1–20% of the total solid weight of the composition.

9. The composition of claim 1, wherein the composition is present in a unit dosage form.

10. The composition of claim 9, wherein the unit dosage form is selected from the group consisting of a gelatin capsule and a tablet.

11. The composition of claim 1 wherein the lipophilic substance is a drug.

12. The composition of claim 1 wherein the lipophilic substance is selected from the group consisting of a vitamin and hormone.

13. The composition of claim 1 wherein the lipophilic substance is selected from the group consisting of a steroid, steroid antagonist, non-steroidal anti-inflammatory agent, antifungal agent, antibacterial agent, antiviral agent, anti-cancer agent, anti-hypertensive agent, anti-oxidant agent, anti-epileptic agent and anti-depressant agent.

14. The composition of claim 1 wherein the lipophilic substance is selected from the group consisting of dexanabinol, etoposide, coenzyme Q10, melatonin, amphotericin, tamoxifen and tamoxifen methiodide.

15. A method for preparing the solid coprecipitate of claim 1, comprising:

comelting the TPGS and the lipophilic substance at about 40°–60° C.;

adding the dispersion adjuvant to the melted mixture with agitation; and drying the resultant mixture to obtain a dry coprecipitate.

16. The method of claim 15 in which the drying is achieved by spray drying or freeze drying of the mixture.

17. The method of claim 15 wherein the dispersion adjuvant comprises a solution of a polyvinylpyrrolidone.

18. The method of claim 15 which further comprises adding fumed silica to the mixture of TPGS, lipophilic substance and dispersion adjuvant with agitation.

19. A method for delivering a lipophilic substance to a mammal in need of such a substance which comprises orally administering a therapeutically effective amount of the solid coprecipitate of claim 1.

20. The method of claim 19 wherein said coprecipitate is administered to a mammal having brain damage, periodontal disease, a blood circulation disease, impaired memory, fatigue, an irregular heartbeat, an immune system impairment, aging, a sleep disorder, a mood disorder, a migraine, or a fungal condition.

21. The method of claim 20 wherein the blood circulation disease is high blood pressure or the fatigue is jet lag.

22. The method of claim 19 wherein the coprecipitate comprises as the lipophilic substance an agent selected from the group consisting of dexanabinol, etoposide, coenzyme Q10, melatonin, amphotericin, tamoxifen and tamoxifen methiodide.

* * * * *